United States Patent [19]

Keyes

[11] Patent Number: 4,714,677

[45] Date of Patent: Dec. 22, 1987

[54] PROTEIN MODIFICATION TO PROVIDE ENZYME ACTIVITY

[75] Inventor: Melvin H. Keyes, Sylvania, Ohio

[73] Assignee: Owens-Illinois Glass Container Inc., Toledo, Ohio

[21] Appl. No.: 477,553

[22] Filed: Mar. 21, 1983

Related U.S. Application Data

[63] Continuation of Ser. No. 418,884, Sep. 16, 1982, abandoned.

[51] Int. Cl.[4] .................... C12N 9/00; C12N 11/10; C12N 9/14
[52] U.S. Cl. .................................. 435/183; 435/177; 435/178; 435/195; 530/402; 530/813
[58] Field of Search ............. 435/183, 184, 188, 199, 435/200, 201, 213, 178, 177, 195; 260/112, 121; 530/350, 362, 402, 813

[56] References Cited

U.S. PATENT DOCUMENTS 4,366,030 5/1981 Tschang et al. .................... 435/188
4,609,625 9/1986 Keyes et al. ................... 435/188 X

OTHER PUBLICATIONS

Battelle Report, Varification of Semisynthetic Activity, Owens–Illinois, Jul. 14, 1981.
Yamauchi et al., Reversible Conversion of Lysime Monooxygenase to an Oxidase,; *J. of Biol. Chem*, vol. 248, 1973, pp. 3750–3752.
Mahler et al., *Biological Chemistry*, 1966, Harper and Row N.Y. pp. 287–295.
Beaven et al., *International Journal of Peptide Research*, vol. 5, pp. 215–218, 1973.

*Primary Examiner*—David M. Naff
*Attorney, Agent, or Firm*—H. G. Bruss

[57] ABSTRACT

A naturally occurring protein is chemically modified to provide the protein with activity of a selected enzyme. The protein does not contain activity of the selected enzyme before modification. Modification is carried out by partially denaturing the protein, contacting the partially denatured protein with an immobilized enzyme inhibitor of the selected enzyme, crosslinking the protein in the presence of the inhibitor and recovering a modified protein having activity of the selected enzyme.

30 Claims, No Drawings

PROTEIN MODIFICATION TO PROVIDE ENZYME ACTIVITY

This is a continuation of application Ser. No. 418,884 filed Sept. 16, 1982, now abandoned.

BACKGROUND OF THE INVENTION

1. Field of the Invention

Proteins are biologically synthesized macromolecules having various roles in living systems. Enzymes are particular varieties of biologically active proteins which catalyze specific reactions. Presently, enzyme technology is used in many areas in industry and research such as, for example, medical research, food processing and preservation, the production of fermented beverages, the production of pharmaceuticals and the analytical determination of the concentration of various metabolites and food components by analytical enzyme techniques.

Enzymes are highly specific in their biological activity and generally catalyze a particular reaction at a very high rate compared to the corresponding reaction occurring at room temperature without biological catalysis. One enzyme may show catalytic activity with respect to a number of well defined substrates upon which it can act. Accordingly, a given enzyme may catalyze the synthesis or degradation of more than one substrate. Some proteins which are not considered classical enzymes, such as bovine serum albumin, show very limited catalytic activity with respect to one or more substrates.

Many enzymes are found in nature in very small quantities. Accordingly, their isolation, purification and use is limited to a small scale operation in view of the expense and time needed to isolate them in a useful form.

Some enzymes occur in nature in relatively-large quantities and are relatively easy to isolate, purify and use. Unfortunately, due to the precise catalytic behavior of the enzymes, the enzymes available in large quantities can only catalyze certain select reactions.

Much effort has been directed in the recent past toward the synthesis of synthetic biological catalysts which exhibit enzymatic behavior similar to enzymatic behavior exhibited by native enzymes which are either scarce or expensive to isolate. Further, some attempts have been made to modify native enzymes to change their enzymatic specificity so that they may function to catalyze a reaction which they previously could not catalyze.

2. Description of the References

One technique known to achieve enzyme behavior to catalyze a specific desired reaction is the synthesis of so-called enzyme model molecules. For example, low molecular weight compounds may be covalently bonded to functional groups which exhibit the activity of the active site of an enzyme. Examples of such preparations are described in the publications: Breslow, R., *Advances in Chemistry Series*, R. F. Gould, Ed., American Chemical Society, Washington, D.C. 21-43 (1971) and Tang, C. C.; Davalian, D.; Haung, P. and Breslow, R., *J. Amer. Chem. Soc.*, 100, 3918 (1978).

Another technique involves the use of a synthetic polymer matrix which is modified along its backbone to provide functional groups which exhibit the function of the active site of a given enzyme. Examples of such techniques can be found in the following articles: Wulff, G. and Schulza, I., *Israel J. Chem.*, 17, 291 (1978) and Suh, J. and Klotz, I. M., *Bioorganic Chemistry*, 6, 165 (1977).

Another technique involves the attachment of a new chemical moiety to a native enzyme near the active site of the enzyme to attempt to cause such enzyme to react with a different catalytic activity. One example of this is the conversion of papain, a proteolytic enzyme to an oxidase type enzyme by the covalent attachment of a flavin near the active site of the native papain enzyme, as illustrated in the articles: Levine, H. L. and Kaiser, E. T., *J. Amer. Chem. Soc.*, 100, 7670 (1978), Kaiser, E. T., et al, *Adv. In Chemistry Series*, No. 191, Biomimetic Chemistry, page 35, 1980; and Otsuki, T.; Nakagawa, Y. and Kaiser, E. T., *J.C.S. Chem. Comm.*, 11, 457 (1978). Other examples of such enzymatic modification may be found in the article: Wilson, M. E. and Whitesides, G. M., *J. Amer. Chem. Soc.*, 100, 306 (1978).

Still another attempt to change enzyme specificity is the immobilization of a native enzyme into a gel matrix. For example, trypsin enzyme has been immobilized in polyacrylamide gel. The polyacrylamide gel allows amino acid esters to diffuse through the gel matrix to react with the enzyme but will not allow larger proteins to diffuse through. Thus, the enzyme specificity is changed by eliminating access of one of the substrate molecules to the enzyme. Examples of such specificity changes are described in the Kirk-Othmer *Encyclopedia of Chemical Technology*, 3 Ed., 9, 148 (1980) published by Wiley and Son, Inc.

Also, it has been known that a native lysine monooxygenase can be reacted to block the sulfhydryl groups on the enzyme. When the specific enzyme lysine monooxygenase is so treated, it shows new catalytic activity toward amino acids and catalyses oxidative deamination instead of its natural oxygenative decarboxylation. However, the reporters cannot account for the modified behavior. See the article by Yamauchi, T.; Yamamoto, S. and Hayaishi, O., in *The Journal of Biological Chemistry*, 248, 10, 3750-3752 (1973). Also, it has been reported that by reacting a native enzyme, for example trypsin, with its natural inhibitor, and subsequently cross-linking the enzyme, its activity with respect to its natural substrates can be modified. See the article by Beaven, G. H. and Gratzer, W. B. in *Int. J. Peptide Res.*, 5, 215-18 (1973).

Also, synthetic proteins have been synthesized by the anchoring of an amino acid residue on a solid support and subsequently adding amino acid residues one after another.

Further, semisynthetic proteins have been synthesized by a method wherein a native protein is subjected to limited hydrolysis to produce protein fragments. The fragments of the native protein are then subjected to a process whereby one or more amino acid residues are added or removed from the fragments to form modified fragments. The resultant modified fragments are then reattached to form the semisynthetic protein with an altered amino acid residue composition. Examples of the synthetic and semisynthetic protein technologies cited immediately above are found in the book *Semisynthetic Proteins* by R. E. Offord, published by John Wiley and Sons Ltd., copyrighted in 1980.

While these techniques are suitable for many applications, a need exists for a simple, efficient, and economical method for chemically modifying an inexpensive and commercially available native protein to produce a modified enzyme-like protein which shows an activity with respect to a desired chemical reaction which was not previously a commercially-useful reaction catalyzed by the native enzyme and which a new reaction can be predetermined in a systematic fashion. The methods disclosed in the above-described references simply subject an enzyme to a set of conditions and attempt to eludicate its behavior. They fail to present a systematic method to modify protein.

SUMMARY OF THE INVENTION

The present invention achieves a modified protein with enzyme-like characteristics by subjecting a naturally occurring so called native protein to partial denaturation by exposure to a denaturing agent, to partly unfold the conformational structure of the native protein. Next, an inhibitor of the model enzyme, whose activity is to be modeled, is selected and the inhibitor is immobilized on a solid support. Next, the partially denatured native protein is contacted with the immobilized inhibitor of the model enzyme. Subsequently, the partially denatured native protein in the presence of the inhibitor is cross-linked to define a new modified protein. Then the immobilized inhibitor and any excess cross-linking agent are removed from the newly formed modified enzyme-like protein to yield a functional analogue to the model enzyme. The modified enzyme-like protein thusly produced exhibits activity characteristic of the model enzyme.

DETAILED DESCRIPTION OF THE INVENTION

In attaining the objects and advantages of the present invention, it has now been discovered that a protein can be modified from its native conformation to a modified enzymatically active conformation by practicing the process of the present invention.

As used herein, the word "enzyme" is defined as a protein which has well known catalytic activity toward specific substrates. The term "protein" as used herein is defined as generally accepted in the art, to wit, a polypeptide formed of amino acids to yield a biological molecule.

The present invention comprises process for modifying a native protein from one conformation to a second conformation. The modification process produces a modified enzyme-like protein which models one or more characteristics of selected model enzymatic protein. In the preferred embodiment a nonenzymatic native protein is converted by the process of the invention into a modified enzyme-like protein having the activity characteristics of the model enzyme.

The preferred embodiment of the present invention comprises a process for modifying a native protein from one conformation to a second conformation and thereby producing a new enzymatically active modified protein from the selected native protein. Alternatively, a marginal enzymatic activity present in the native enzyme can be increased to a commercially useful level by practicing the process of the present invention.

The process of the present invention comprises the preparation and use of an immobilized inhibitor agent and a partially denatured protein to produce a modified protein, which exhibits enzyme-like catalysis characteristics. In the preferred embodiment an enzyme to be modeled is selected. Next an inhibitor for this predetermined enzyme is identified. The inhibitor of the enzyme to be modeled is immobilized on a solid support.

A native protein is selected which is to be converted into a modified enzyme-like protein. The native protein is purified and partially denatured. After the native enzyme is partially denatured, it is contacted with the immobilized inhibitor. Sufficient time and temperature is provided for an amount of the partially denatured native protein to bind to the immobilized inhibitor. Next the excess, unbound partially denatured native protein is washed off the solid support containing the inhibitor.

The partially denatured native protein remaining bound to the immobilized inhibitor is cross-linked. Then the excess cross-linking agent is washed off the immobilized inhibitor. The inhibitor-bound, cross-linked, protein is selectively washed off the immobilized inhibitor to yield a modified enzyme-like protein showing the catalytic characteristics of the model enzyme whose inhibitor was used in the process.

As used herein, immobilized inhibitor means an inhibitor that is strongly attached to a solid, preferably water insoluble support, such that the inhibitor is substantially water insoluble during all steps of the present process.

In the preferred embodiment the inhibitor is covalently bonded to a water insoluble support. The support may be organic or inorganic. One such water insoluble organic support is a cross-linked, beaded, high molecular weight polysaccharide which has been cross-linked with epichlorohydrin. Such a material is commercially available under the name Sephadex, marketed by Pharmacia Fine Chemicals.

Another preferred solid organic water insoluble support is an agarose based, linear, cross-linked polysaccharide having alternating residues of D-galactose and 3, 6 anhydro-L-galactose. Such a material is commercially available under the name Sepharose, marketed by Pharmacia Fine Chemicals.

Still another preferred solid support which is organic and water insoluble is a three dimensional polyacrylamide lattice having an interstatial agarose gel. Such a material is commercially available under the name Ultrogel and is marketed by LKB Produkter, AB of Stockholm, Sweden.

Preferred inorganic water insoluble supports include refractory ceramic oxides. Suitable ceramic oxides include porous, particulate ceramic oxides which can be formed by compacting and sintering refractory ceramic oxide powders such as alumina powder, zirconia powder, magnesia powder, silica powder and thoria powder. The preparation and use of such ceramic oxide supports is disclosed in U.S. Pat. No. 4,001,085.

As defined herein, "partial denaturation" means a change in the conformation of a protein so as to perturb the shape or conformation of the protein without causing an irreversible, gross denaturation of the protein. "Conformation" is defined, as generally accepted in the art, as that combination of secondary and tertiary structure of a protein. The partial denaturation of proteins is well known and discussed in detail in the following references: the book *Biochemistry*, by A. L. Lehninger, Worth Publishers, Inc., N. Y., 1970, pg. 58; the article by P. L. Privalov entitled "Stability of Proteins" in *Advances in Protein Chemistry*, Vol. 33, pg. 167–192; the article by C. Sanford entitled "Protein Denaturation, PART C" in *Advances in Protein Chemistry*, Vol. 24, pg. 2–97; the article by F. R. N. Gurd, et al. entitled "Motions in Proteins": in *Advances in Protein Chemistry*, Vol. 33, pg. 74–166; the article by O. Jardetzky in *BBA*, Vol. 621, pg. 227–232; the article by R. Huber in *TIBS*, Dec.

1979, pg. 271, and the article by D. S. Markovich, et al. in *Molekulyarnaya Biologiya*, Vol. 8, No. 6, pg. 857–863.

As used herein, the phrase "denaturing agent" refers to process conditions or reagents which cause the partial denaturation of a protein. For example, the partial denaturation of a protein can be accomplished by soaking the protein in an aqueous solution at elevated temperatures, for example, in the range of 25° C. to 60° C. For most proteins 25° C. to 60° C. will so perturb the structure of the protein as to result in partial denaturation of the protein. However, as is well known in the art, some proteins from thermophilic bacterial sources are stable to near the boiling point of water, and would require higher elevated temperatures than those generally disclosed above. Also, the partial denaturation of a protein can be accomplished by soaking the protein in an aqueous solution containing a inorganic salt, an inorganic or organic acid or a water-miscible organic solvent.

Suitable inorganic salts which serve to destabilize the protein structure include: $NaF$, $(NH_4)_2SO_4$, $(CH_3)_4NCl$, $(CH_3)_4NBr$, $KCH_3COO$, $NH_4Cl$, $RbCl$, $KCl$, $NaCl$, $CsCl$, $LiCl$, $KBr$, $NaBr$, $KNO_3$, $MgCl_2$, $NaNo_3$, $CaCl_2$, $KSCN$, $NaSCN$, $BaCl_2$, $NaI$, and $LiI$.

Suitable inorganic acids include: hydrochloric, nitric, sulfuric, phosphoric and similar proton donating strong inorganic acids.

Suitable organic acids include: acetic, formic, propionic and citric acid.

Suitable water-miscible solvents, which are believed to solubilize hydrophobic groups on the protein and thereby destabilize its structure, include: t-butanol, acetonitrile, dioxane, acetone, methanol, ethanol and dimethylsulfoxide.

As used herein, the term "inhibitor" means any compound with sufficient structural similarity to the natural substrate to serve as a template for the active site of a modified enzyme-like protein. In the preferred embodiment of the preparation of a modified enzyme-like protein, the inhibitor is any of the known classical inhibitors for a given model enzyme. However, as used herein "inhibitor" can include any molecule with sufficient structural similarity to the classical inhibitor to preserve an inhibitor like site on the modified protein. The natural substrate of the model enzyme can act as inhibitor or template for the modified protein in many cases. One example of the structural similarity of an enzyme inhibitor and the natural substrate of an enzyme is the case of glucose oxidase. Glucose is the natural substrate of glucose oxidase while D-glucal is the inhibitor for glucose oxidase. Glucose and D-glucal are very structurally similar.

As defined herein, the term "cross-linking" means the formation of covalent bonds between reactive sites on a protein. For cross-linking, the process is usually accomplished by the use of multifunctional reagents such as glutaraldehyde. Other examples of suitable cross-linking reagents to effect a cross-linking of a protein are: 2-amino-4, 6-dichloro-s-triazine; diazonium salts; N-hydroxy succinamide; p-benzoylazide and those reagents disclosed in the following references: Wold, F., *Methods Enzymol,* 11; Hirs, C. H. W. editor, Academic Press, 1967, 617; Fasold, H. et al, *Augen. Chem. Int. Ed. Engl.,* 10, 795, 197, and Keyes, M. H., *Kirk-Othmer: Encyclopedia of Chemical Technology,* 9, 3d ed., 1980, J. Wiley and Sons, Inc., 148–172.

Examples of enzymes which are susceptible to modeling by the present process to produce their modified enzyme-like protein analogues from a selected native protein are hydrolytic enzymes, redox enzymes and transferase enzymes. By way of example: The first group, hydrolytic enzymes include proteolytic enzymes which hydrolyze proteins, e.g., papain, ficin, pepsin, trypsin, chymotrypsin, bromelin, keratinase, carbohydrases which hydrolyze carbohydrates, e.g., cellulase, amylase, maltase, pectinase, chitanase; esterases which hydrolyze esters, e.g., lipase, cholinesterase, lecithinase, alkaline and acid phosphateases; nucleases which hydrolyze nucleic acid, e.g, ribonuclease, deoxyribonuclease; and amidases which hydrolyze amines, e.g., arginase, asparaginase, glutaminase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamic-pyruvic transaminase, glutamic-oxalacetic transaminase, transmethylase, phosphopyruvic transphosphorylase.

In the usual practice, one first selects a model enzymatic protein to be modeled. Then one selects a native or second protein to be modeled after the model enzymatic protein to produce a modified enzyme-like protein. In many cases the native protein is an enzymatic protein itself since many common enzymes are available in large quantities at fairly low costs in homogeneous samples. However, nonenzymatic proteins are equally useful when they can be purified for use with the process. Such a protein is bovine serum albumin.

By practicing the process of the present invention, one can custom-tailor the native protein into a different, modified protein which shows the enzymatic activity characteristics of the enzyme which was modeled. The ability to custom-tailor a protein into a predetermined catalytic activity provides great advantages in a wide range of chemical and industrial situations. For example, if the enzyme one wishes to use is in short supply, is very expensive or difficult to purify it may be produced by the present process.

Thus, a native protein which is available in large quantities and/or at low cost can be reformed or modified by the process of the present invention to convert the available protein into a catalytically active modified enzyme-like protein form of the less available and/or more expensive enzymatic protein.

In the preferred embodiment of the present invention, a flow-through column is used to practice the process due to the precise control of flow-through speeds which is available. The support immobilized inhibitor is wet packed into the column so that the following chemical agents may be contacted with the support and the support bound native protein by simply pumping, at a controlled flow rate, various aqueous solutions through the column.

Many water insoluble immobilized inhibitors are available from commercial sources wherein they have been immobilized on polysaccharide supports, inorganic supports and synthetic polymeric supports as described above.

It is also possible to bind the inhibitor to a water soluble support like a protein, such as serum albumin. In such case the inhibitor is immobilized on the protein but remains in water soluble form. Such soluble, immobilized inhibitors can be trapped in a flow-through column, as described above for use, by placing ultrafiltration membranes at both ends of the column to keep the soluble inhibitor-support unit in place. The native protein is pumped through the membrane and into contact with the membrane trapped immobilized, soluble inhibitor.

In some cases where the native protein to be modified contains large numbers of disulphide bridges, for example, bovine serum albumin or urease, the partial denaturation may be effected by breaking disulphide linkages within the protein by subjecting the protein to mercaptoethanol, or other sulfhydryl reduction reagent which cleave disulfide bonds.

When the native protein has been partially denatured, a solution of the partially denatured protein is flowed through the column slowly, usually at about one milliliter per minute when the concentration of the native protein is about one percent by weight and the column is about 7.5 centimeters in length and about 1.5 centimeters interior diameter. An aliquot of about two milliliters of the about one percent solution is typically injected onto the column. As the partially denatured native protein flows through the column of immobilized inhibitor the protein is believed, without being limited by any mechanistic theory, to bind to the inhibitor and allow a portion of the protein to mold to the shape of the inhibitor. Thus the inhibitor acts as a template for the formation of a new geometry on the partially denatured protein which was not formerly present. While not wishing to be bound by any theory, it is believed that the advantageous results of the present invention are obtained because the partial denaturation of the native protein results in a loosening of the protein structure. The loosened protein structure allows the inhibitor to bind to the protein and define a new molecular structure on the partially denatured native protein complementary to the inhibitor shape.

After the contacting or binding of the partially denatured native protein to the immobilized inhibitor, to create a new structure on the surface of the protein complementary to the shape of the inhibitor, the partially denatured native protein must be stabilized to preserve the new site. The new shape of the protein is stabilized by cross-linking. Often, the cross-linking is done with glutaraldehyde cross-linking agent since it is relatively inexpensive. However, any of the above-described cross-linking agents can be utilized effectively.

The cross-linking in the preferred embodiment is conducted by flowing a solution of the cross-linking agent through the column bearing the inhibitor bound protein in a recirculating fashion Usually a low speed, low volume pump is connected to a reservoir from which it draws cross-linking agent solution. The solution is pumped through the column and reservoir loop for about one and a half hours. Typically about twenty microliters of eight percent by weight glutaraldehyde is added to the circulating solution when the column is fully packed and about eight centimeters in length and about two centimeters in diameter.

After the cross-linking agent solution is recirculated through the column for the desired time, the column is charged with an eluant which will desorb the newly formed, stabilized enzyme-like modified protein enzyme from the solid support. An acidic solution of glycine has been useful for this purpose.

The column effluent is monitored spectrophotometrically, in the ultraviolet range, to detect modified protein elution. The amount of collected modified protein is determined by spectral analysis to ascertain yield. The enzymatic activity of the newly produced modified enzyme-like protein is determined by any conventional enzyme kinetics method.

In an alternative embodiment of the present process the native protein can be admixed with the immobilized inhibitor prior to partial denaturation. Subsequently, the denaturing agent is added to the native protein-inhibitor mixture. This embodiment of the invention provides inhibitor availability immediately upon the partial denaturation of the native protein. Then, the partially denatured inhibitor bound protein is cross-linked.

The process of a preferred embodiment in the present invention produces new, enzymatically active modified protein and exhibits a number of advantages. By the discovery that an immobilized inhibitor can be employed one can now use minimal amounts of inhibitor, which amounts are essentially recyclable as the inhibitor is not discarded to purify the modified enzyme-like protein. Rather, fairly inexpensive eluants are used to wash the final product from the immobilized inhibitor, thus preserving expensive inhibitor.

Also, when immobilized inhibitor is used in a flow through system it is easily determined if the partially denatured native protein is binding to the inhibitor.

If the particular native protein does not bind to the inhibitor, the native protein will flow through the column and can be easily detected at the outlet of the column. Were the inhibitor solubilized into an aqueous solution, an entire procedure would have to be conducted to determine if the partially denatured protein had in fact bound t the inhibitor. This could lead to the waste of reagents and purified starting native protein.

Further, by immobilizing the inhibitor, it is possible to introduce a controlled amount of inhibitor onto the water insoluble support. By choosing the loading fraction, for example, a light loading of inhibitor onto the support, the extent of oligomer formation in the final modified protein product can be controlled. When the support is sparsely coated with immobilized inhibitor the probability of dimer, trimer or oligomer formation, due to adjacently located native protein molecules being intermolecularly cross-linked is decreased. Generally, the formation of oligomers is not desired since such protein aggregates often show low water solubility and are not easily purified and handled.

Additionally, with the use of immobilized inhibitor in a flow through system there is no need to employ complex separation techniques to separate the cross-linking agent from the native protein starting material and the final modified protein from the inhibitor. This ease of material handling also reduces the time for performing the entire process. This is advantageous in view of the fact that many proteins and enzymes which could be selected as the native starting material are temperature and oxygen sensitive. If conventional separation techniques were employed to separate various materials from one another this would lengthen the process and lower yields due to oxidative degradation and thermal degradation. To militate against such problems low temperatures and inert atmosphere techniques, at added cost, would be needed to preserve yields.

For convenience of disclosure, all patent documents and publications mentioned herein are incorporated by reference.

Other embodiments of the invention will be apparent to those of ordinary skill in the art from a consideration of this specification or practice of the invention disclosed herein. It is intended that the Examples and specifications be considered as exemplary only, with the scope and spirit of the invention being indicated by the claims. The following Examples are exemplary of the process of the present invention.

EXAMPLE 1

PART A

Preparation of Immobilized Model Enzyme Inhibitor Column

A glass walled chromatography column of about 7.5 centimeters length and about 1.5 centimeters interior diameter is used in the procedure. An immobilized inhibitor, L-tryptophanagarose gel, purchased from Sigma Company, No. T-0137, lot 80F-9610, is stored in 0.5M NaCl solution, at about zero degrees centigrade until used.

To prepare the column for acceptance of the native protein, the column is packed about 3.8 cm. high with immobilized inhibitor. After the column is packed, the column is purged of possible contaminants as follows: A 200 milliliter aliquot of distilled water is flushed through the column at a rate of one milliliter per minute. Next, 500 milliliters of 0.1M carbonate buffer, containing 0.5M NaCl, at pH 10 is flushed through the column at one milliliter per minute. Next, 500 milliliters of 0.1M sodium acetate buffer, at pH 4.0 containing 0.5M NaCl is flushed through the column at one milliliter per minute. A final five hundred milliliter wash of 2.0 molar urea solution is flushed through the column.

PART B

Partial Denaturation of the Protein & Binding to the Inhibitor

A fresh one percent solution of bovine serum albumin (BSA) is prepared by dissolving 0.2 grams of bovine serum albumin essentially fatty acid free, from Sigma Company, No. A 7511, lot 90F-9315 in 20 milliliters of distilled water. The absorbance of the fresh BSA is determined in accordance with the teachings of D. M. Kirschenbaum in *Int. J. Peptide Res*, 5, 1973, pages 49–62. The absorbance at 280 nm is measured and is 6.43. Using the absorbance coefficient of 6.62 for a one percent solution, the concentration of the solution is about 9.7 milligrams per milliliter.

The column of PART A is filled with a flowing stream of 0.01M acetate buffer at pH 4.4 flowing at one milliliter per minute, which acts as the denaturing agent solution. Two milliliters of the on percent BSA solution is injected at the head of the column. By so injecting, the BSA is brought to a lowered pH and under such low pH, partially denatured as it is applied to the column.

The eluant from the column is monitored at 254 nm. When that portion of the BSA not binding to the immobilized inhibitor eluted from the column, it is collected and is determined by absorbance at 280 nm. to contain about 16 milligrams. Accordingly, about 3.4 milligrams of the BSA is bound to the inhibitor on one exposure to the column.

PART C

Cross-Linking

The outlet of the column of PART B is connected to a recirculating pump. The outlet of the pump is connected to the head of the column, thus forming a closed recirculation flow loop. Next 20 microliters of eight percent glutaraldehyde from Polysciences, Inc., Cat. No. 216, lot 4-1462, is added to 25 milliliters of the acetate buffer at pH 4.4. The glutaraldehyde solution is injected onto the column and recirculated for about 90 minutes.

PART D

Collection of the Modified Protein

The recirculating system of PART C is disconnected and a 0.02M glycine-HCl buffer at pH 3.0 is pumped through the column now containing the inhibitor bound, stabilized modified enzyme-like protein, at one milliliter per minute. After about 15 minutes, modified protein began eluting from the column. About twenty-four milliliters of eluant is collected before the modified protein stopped eluting from the column. The collected modified protein is raised from pH 3 to about pH 6.9 to stabilize the protein structure, by the addition of one milliliter of 0.1M tris buffer, pH 7.5, to nine milliliters of eluant. A total of about 0.3 milligrams of modified protein is collected.

PART E

Results

The following activity with respect to substrate for esterase enzyme is recorded from a sample of modified esterase-like protein prepared according to the invention.

A portion of the eluant solution of modified protein is analyzed for esterase enzymatic activity by high pressure liquid chromatography as follows:

The assay sample is prepared as follows: Sixteen milliliters of 0.1M tris buffer, pH 7.7, and 2 milliliters of 0.1M N-alpha-benzoyl-L-arginine ethyl ester (BAEE) substrate are mixed with 2 milliliters of modified protein.

The control solution is made by adding 16 milliliters of 0.1M tris buffer, pH 7.7 to 2 milliliters of 0.1 M BAEE and 2 milliliters of 0.02M glycine-HCl which is the column eluant which is adjusted to pH 6.9 with tris buffer at pH 7.5.

The high pressure liquid chromatography column conditions for the assay are as follows: The column is packed with CM glycophase support from Pierce Chemical Co. Product No. 23512, which is a hydrophilic, nonionic carbohydrate layer containing carboxyl methyl side chains covalently bound to controlled pore size glass. The particle size is about 125–177 microns and the pore size is about 200 angstroms. The column eluant is 0.005M tris buffer, at pH 8.1, containing 0.05M NaCl. The flow rate is 1.75 milliliters per minute for a 27 centimeter by 0.3 centimeter column. Twenty microliters of sample is in3ected and the peak height for the benzoyl-L- arginine determined at 254 nm. is recorded. Next, the control is injected. After collecting at least four data points for both sample and control, the activity is calculated from a plot of the concentration of benzoyl-Larginine versus time. The assay results are as follows:

|  | Substrate<br>BAEE (U/gm) |
|---|---|
| Initial Activity | 0.00 |
| Final Activity | 0.18 |

The results show that the modified esterase-like protein of PART D exhibits activity with respect to the esterase substrate BAEE where no activity is previously detected in the 1 native BSA protein. This illustrates the conversion of one genus of nonenzymatic protein, an albumin, to another genus of protein, an enzymatically active esterase-like protein.

To illustrate that native BSA protein shows no detectable catalytic activity with respect to BAEE substrate the test procedure disclosed in Example 3 is performed. The result illustrates that BSA shows no detectable catalytic activity with respect to esterase substrate BAEE.

EXAMPLE 2

PART A

Preparation of Immobilized Model Enzyme Inhibitor Column

A glass walled chromatography column of about 7.5 centimeters length and about 1.5 centimeters interior diameter is used in the procedure. An immobilized inhibitor, L-arginineagarose gel, purchased from Sigma Company, No. A-1018, Lot 20F-9740, is stored in 2.0M NaCl solution at about zero degrees centigrade until used.

To prepare the column for acceptance of the native protein, the column is packed about 4 centimeters high with immobilized inhibitor. After the column is packed, the column is purged of possible contaminants as follows: A 200 milliliter aliquot of distilled water is flushed through the column at a rate of one milliliter per minute. Next, 500 milliliters of 0.1M carbonate buffer, containing 0.5M NaCl, at pH 10 is flushed through the column at one milliliter per minute. Next, 500 milliliters of 0.1M sodium acetate buffer, at pH 4, containing 0.5M NaCl is flushed through the column at one milliliter per minute. A final five hundred milliliter wash of 2 molar urea solution is flushed through the column.

PART B

Partial Denaturation of the Protein and Binding to the Inhibitor

A fresh one percent solution of bovine serum albumin, (BSA) is prepared by dissolving 0.1 grams of fatty acid free, fraction V bovine serum albumin, from Sigma Company, No. A-6003, lot 110F-9305 in 10 milliliters of distilled deionized water. The aabsorbance of the BSA solution is determined in accordance. with the teachings of D. M. Kirschenbaum in *Int. J. Peptide Res,* 5, 1973, pages 49–62. The absorbance at 280 nm is measured and is 6.83. Using the absorbance coefficient of 6.62 for a one percent solution, the concentration of the solution is about 10.3 milligrams per milliliter.

Prior to addition of the BSA to the column, 0.2 milliliters of 0.1M 2-mercaptoethanol, in distilled deionized water, is added to 10 milliliters of the one percent BSA solution. The partial denaturation is allowed to continue for about one hour at room temperature.

A 0.001M tris buffer, at pH 7, is pumped through the column at one and one-half milliliters per minute. Three milliliters of the BSA solution is injected onto the column at the flow rate of one and one-half milliliters per minute. A total of about 30.9 milligrams of BSA is applied to the column.

PART C

Cross-Linking And Collection of Modified Protein

A cross-linking solution is prepared by dissolving about 0.14 grams of dimethyl suberimidate dihydrochloride cross-linking agent in twenty-five milliliters of 0.001M tris buffer, pH 7.0. The outlet of column of PART B is connected to a recirculating pump. The outlet of the pump is connected to the head of the column, thus forming a closed recirculation flow loop. Next, cross-linking agent is recirculated through the column for three hours at a flow rate of one milliliter per minute.

The circulating cross-linking agent solution is found to contain approximately 15 milligrams of the modified protein originally bound to the column, thereby leaving 15 milligrams still bound.

The recirculating system is disconnected and an eluant is changed to 0.02M glycine-HCl buffer at pH 2.5 to collect the residual modified protein bound to the column.

After pumping the 0.02M glycine-HCl buffer at pH 2.5 at a flow rate of one and one-half milliliters per minute for approximately 15 minutes, modified protein began eluting from the column. About 20 milliliters of eluant is collected before the modified protein stopped eluting.

The absorbance at 280 nm is determined as in PART B to be 0.432 thus about 13 milligrams of modified protein is found to be collected.

PART D

Results

The following activity with respect to substrate for esterase enzyme is recorded from a sample of modified esterase-like protein prepared according to the invention and collected in PART C, above.

A portion of the eluant solution of modified protein is analyzed for esterase enzymatic activity by high pressure liquid chromatography.

The high pressure liquid chromatography column conditions for the assay are as follows: The column is packed with CM glycophase support from Pierce Chemical Company, which is a hydrophilic, nonionic carbohydrate layer containing carboxyl methyl side chains covalently bound to controlled pore size glass. The particle size is about 125–177 microns and the pore size is about 200 angstroms. The column eluant is 0.005M tris buffer at pH 8.0, containing 0.01M NaCl. The flow rate is 8.5 milliliters per minute.

The assay sample is prepared as follows: Fourteen milliliters of 0.01M tris buffer, pH 7.7, and 2 milliliters of 0.1M N-alpha-benzoyl-L-arginine ethyl ester (BAEE) substrate are mixed with 4 milliliters of modified protein collected from column of PART C, above. The control solution is made by adding 14 milliliters of 0.01M tris buffer, pH 7.7 to 2 milliliters of BAEE (0.1M), and 4 milliliters of 0.02M glycine-HCl buffer at pH 2.5. After mixing, the pH of the assay sample and control solution is found to be 7.5.

Twenty microliters of sample is injected into the above high pressure liquid chromatography column. Elution is done as described above and the peak height for the benzoyl-L-arginine detected at 254 nm is recorded. Next, the control is injected and the benzoyl-L-arginine peak height recorded. After collecting at least five data points for both sample and control, the activity is calculated from a plot of the concentration of benzoyl-L-arginine versus time using linear regression analysis.

To determine initial activity, native BSA, from Sigma Chemical Company, A-6003, Lot No. 110OF-9305, is assayed against BAEE substrate for potential enzymatic activity. The native BSA solution is prepared by dissolving 0.013 grams of BSA in twenty milliliters of 0.02M glycine-HCl buffer, pH 2.5. The BSA solution has an absorbance at 280 nm of 0.453. Using the absorbance coefficient of 6.62 for a one percent solution, the concentration is calculated to be 0.68 milligrams per milliliter. The native BSA assay solution is prepared as follows: Fourteen milliliters of 0.01M tris buffer, pH 7.7; two milliliters of 0.1 M BAEE and four milliliters of native BSA solution. The control solution is prepared by mixing 14 milliliters of 0.01 M tris buffer, pH 7.7 to 2 milliliters of 0.1M BAEE and 4 milliliters of 0.02M glycine-HCl buffer, pH 2.5. After mixing, the pH of the native BSA assay solution and control solution is 7.5. Twenty microliters of native BSA assay solution is injected and the peak height for the benzoyl-L-arginine detected at 254 nm is recorded. Next, the control solution is injected.

After collecting at least five data points for both native BSA assay solution and control, the activity is calculated from a plot of the concentration of benzoyl-L-arginine versus time using linear regression analysis. The assay results show that the slope of the native BSA assay solution is $2.48 \pm 0.11 \times 10^{-7}$ moles/minute and the slope of the control is $2.59 \pm 0.04 \times 10^{-7}$ moles/minute, which indicates that there is no detectable native esterase activity toward BAEE substrate present in the native BSA.

The calculated activity from the assay results for the modified esterase-like protein is as follows:

|  | Substrate BAEE (U/gm) |
|---|---|
| Initial Activity | 0.00 |
| Final Activity | 0.813 ± 0.146 |

The results show that the modified esterase-like protein of PART C exhibits activity with respect to the esterase substrate BAEE where no activity is previously detected in the native BSA protein. This illustrates the conversion of one genus of nonenzymatic protein, an albumin, to another genus of protein, an enzymatically active esterase-like protein.

EXAMPLE 3

PART A

Preparation of Immobilized Model Enzyme Inhibitor Column

A glass walled chromatography column of about 7.5 centimeters length and about 1.5 centimeters interior diameter is used in the procedure. An immobilized inhibitor, L-tryptophanagarose gel, purchased from Sigma Company, No. T-0137, lot 80-F-9610, is stored in 0.5M NaCl solution at about zero degrees centigrade until used.

To prepare the column for acceptance of the native protein, the column is packed about 3.8 cm. high with immobilized inhibitor. After the column is packed, the column is purged of possible contaminants as follows: A 200 milliliter aliquot of distilled water is flushed through the column at a rate of one milliliter per minute. Next, 500 milliliters of 0.1M carbonate buffer, containing 0.5M NaCl, at pH 10 is flushed through the column at one milliliter per minute. Next, 500 milliliters of 0.1M sodium acetate buffer, at pH 4, containing 0.5M NaCl is flushed through the column at one milliliter per minute. A final five hundred milliliter wash of 2 molar urea solution is flushed through the column.

PART B

Partial Denaturation of the Protein & Binding to the Inhibitor

A fresh one percent solution of bovine serum albumin (BSA) is prepared by dissolving 0.2 grams of bovine serum albumin essentially fatty acid free, from'Sigma Company, No. A 7511, lot 90F-9315 in 20 milliliters of distilled water. The absorbance at 280 nm is measured and is 6.22. The concentration of the BSA solution is determined in accordance with the teachings of D. M. Kirschenbaum in *Int. J. Peptide Res*, 5, 1973, pages 49–62. Using the absorbance coefficient of 6.62 for a one percent solution, the concentration of the solution is about 9.4 milligrams per milliliter.

The column of PART A is filled with a flowing stream of 0.01M acetate buffer at pH 4.0 flowing at one milliliter per minute, which acts as the denaturing agent solution. Two milliliters of the one percent BSA solution is injected at the head of the column, thus about 18.8 milligrams of BSA were added to the column. By so injecting, the BSA is brought to a lowered pH and under such low pH, partially denatured as it flowed onto the column.

The eluant from the column is monitored at 280 nm. When that portion of the BSA not binding to the immobilized inhibitor eluted from the column, it is collected and by the above method, is determined to contain about 17.25 milligrams. Accordingly, about 1.6 milligrams of the BSA is bound to the inhibitor on one exposure to the column.

PART C

Cross-Linking and Collection of Modified Protein

A cross-linking solution is prepared by dissolving about 0.068 grams of dimethyl suberimidate dihydrochloride crosslinking agen in fifty milliliters of 0.01M acetate buffer at pH 4.0. The outlet of the column of PART B is connected to a recirculating pump. The outlet of the pump is connected to the head of the column to form a closed recirculaton flow loop. Next, cross-linking agent is recirculated through the column for two hours at a flow rate of one milliliter per minute.

The recirculating system is disconnected and an eluant of 0.02M glycine-HCl buffer at pH 3 is pumped through the column to collect any modified protein bound to the column.

PART D

Results

The following activity with respect to substrate for esterase enzyme is recorded from a sample of modified esterase-like protein prepared according to the invention.

A portion of the eluant solution of modified protein from PART C is analyzed for esterase enzymatic activity by high pressure liquid chromatography as follows:

The assay sample is prepared as follows: Fourteen milliliters of 0.01M tris buffer, pH 8.0, and 2 milliliters of 0.1M N-alpha-benzoyl-L-arginine ethyl ester (BAEE) substrate are mixed with 4 milliliters of modified protein.

The control solution is made by adding 14 milliliters of 0.01M tris buffer, pH 8.0 to 2 milliliters of 0.1M BAEE and 4 milliliters of 0.02M glycine-HCl, pH 3.0, which is the column eluant. The frnal pH of both the assay and the control solution is 7.7

Native BSA, also Sigma Chemical Company, A-7511, Lot No. 90F-9315, is assayed against BAEE esterase substrate to determine initial activity. The native BSA is prepared by dissolving 0.1 grams of BSA in ten milliliters of distilled deionized water. The resultant one percent solution is dialyzed in 0.02M glycine-HCl buffer, pH 3 for two hours. Next, one milliliter of the dialyzed solution of BSA is diluted 1:50 with 0.02M glycine-HCl buffer, pH 3 to give an absorbance at 280 nm of 0.119. The protein concentration is calculated to be 0.18 milligrams per milliliter. The native BSA assay solution is as follows: Fourteen milliliters of 0.01M tris buffer, pH 7.7; two milliliters of 0.1M BAEE and four milliliters of native BSA solution are mixed together to form a solution. The control solution is prepared by mixing 14 milliliters of 0.01M tris buffer, pH 7.7 to 2 milliliters of BAEE (0.1M) and 4 milliliters of 0.02M glycine-HCl buffer, pH 3.

After mixing, the pH of the native BSA and control solution is 7.7. Twenty microliters of native BSA solution is injected and the peak height for the benzoyl-L-arginine detected at 254 nm is recorded. Next, the control solution is injected.

After collecting at least five data points for bot native solution and control, the activity is calculated from a plot of the concentration of benzoyl-L-arginine versus time usin linear regression analysis. The assay results show that the slope of the native BSA is $4.39\pm0.22\times10^{-7}$ moles/min and the slope of the control is $4.69\pm0.17\times10^7$ moles/min. Therefore, this shows that there is no native esterase activity toward BAEE substrate.

The high pressure liquid chromatography column conditions for the assay are as follows: The column is packed with CM glycophase support from Pierce Chemical Co., Product No. 23512, which is a hydrophilic, nonionic carbohydrate layer containing carboxyl methyl side chains covalently bound to controlled pore size glass. The particle size is about 125–177 microns and the pore size is about 200 angstroms. The column eluant is 0.005M tris buffer, at pH 8.0, containing 0.05M NaCl. The flow rate is 4.0 milliliters per minute for a 27 centimeter by 0.3 centimeter column. Twenty microliters of sample is injected and the peak height for the benzoyl-L- arginine detected at 254 nm is recorded. Next, the control is injected. After collecting at least four data points for both sample and control, the activity is calculated from a plot of the concentration of benzoyl-Larginine versus time. The assay results are as follows:

|  | Substrate<br>BAEE (U/gm) |
| --- | --- |
| Initial Activity | 0.00 |
| Final Activity | 17.0 |

The results show that the modified protein of PART D exhibits activity with respect to the esterase substrate BAEE where no activity is previously detected in the native BSA protein. This illustrates the conversion of one genus of nonenzymatic protein, an albumin, to another genus of protein an enzymatically active esterase-like protein.

EXAMPLE 4

PART A

Preparation of Immobilized Model Enzyme Inhibitor Column

A glass walled chromatography column of about 7.5 centimeters length and about 1.5 centimeters interior diameter is used in the procedure. An immobilized inhibitor, L-tryptophan agarose gel, purchased from Sigma Company, No. T-0137, lot 80F-9610, is stored in 0.5M NaCl solution at about zero degrees centigrade until used.

To prepare the column for acceptance of the native glucoamylase enzyme the column is packed about 3.8 cm. high with immobilized inhibitor. After the column is packed, the column is purged of possible contaminants as follows: A 200 milliliter aliquot of distilled water is flushed through the column at a rate of one milliliter per minute. Next, 500 milliliters of 0.1M carbonate buffer, containing 0.5 NaCl, at pH 10 is flushed through the column at one milliliter per minute. Next, 500 milliliters of 0.1M sodium acetate buffer, at pH 4, containing 0.5M NaCl is flushed through the column at one milliliter per minute. A final five hundred milliliter wash of 2 molar urea is flushed through the column.

PART B

Partial Denaturation of the Protein and Binding to the Inhibitor

Five milliliters of glucoamylase, purchased as, amyloglucosidase from Sigma Chemical Co., glucoamylase No. A-3514, lot 28C-0442, with systematic name alpha-1, 4-glucan glucohydrolose, is dialyzed against 0.001M tris buffer, pH 7, overnight. As received from Sigma Chemical Company, 100 mg glucoamylase is suspended in about ten milliliters of 3.2M ammonium sulfate solution, pH 6. The glucoamylase enzyme is dialyzed using a dialysis tubing having a native molecular weight cut-off of 12,000–14,000 daltons.

The absorbance of glucoamylase solution at 280 nm is measured as 9.44. The concentration of the native glucoamylase enzyme is determined in accordance with the teachings of D. M. Kirschenbaum in *Analytical Biochemistry* 82, pages 83–100, 1977. Using the absorbance coefficient value of 13.6, the concentration of the solution is about 6.9 milligrams of enzyme per milliliter of solution.

The column of PART A is filled with a flowing stream of 0.01M acetate buffer at pH 4.0 flowing at one milliliter per minute, which acts as the denaturing agent solution. Two milliliters of the dialyzed native glucoamylase enzyme solution (13.9 milligrams) is injected at the top of the column. By so injecting, the native enzyme is brought to a lowered pH and under such low pH, partially denatured as it flowed onto the column.

The eluant from the column is monitored at 280 nm. When that portion of the enzyme not binding to the immobilized inhibitor eluted from the column, it is collected and by the above method, is determined to contain virtually no partially denatured enzyme. Accordingly, about 13.9 milligrams of the enzyme is bound to the inhibitor on one exposure to the column.

PART C

Cross-Linking And Collection of Modified Protein

A cross-linking solution is prepared by dissolving about 0.034 grams of dimethyl suberimidate dihydrochloride crosslinking agent in twenty-five milliliters of 0.01M acetate buffer at pH 4.0. The output of the column of PART B is connected to a recirculating pump. The output of the pump is connected to the head of the column, thus forming a closed recirculation flow loop. Next, cross-linking agent is recirculated through the column for three hours at a flow rate of one milliliter per minute.

Next, the recirculating system is disconnected and an eluant of 0.01M acetate buffer, pH 4.0 is pumped through the column to establish a stable recorder baseline.

The 0.01M acetate buffer allows a stable baseline to be determined to monitor the elution of the modified protein. After a stable baseline is established the modified protein is eluted with 0.02M glycine-HCl buffer at pH 3 and the entire protein containing fraction is collected.

PART D

Results

The following activity is recorded for a sample of the modified esterase-like protein prepared according to the invention.

A portion of the eluant solutions of modified protein is analyzed for esterase activity by high pressure liquid chromatography and found to have esterase activity. To verify that native glucoamylase shows no esterase activity the following procedure was performed.

Native glucoamylase is assayed against L-tryptopha methyl ester (TME) and shows no natural esterase activity toward the TME.

The native glucoamylase enzyme sample assay is made by adding fourteen milliliters of 0.005M tris, pH 9.1, 4 milliliters of dialyzed native glucoamylase to two milliliters of 0.1M TME. The native glucoamylase is dialyzed against one thousand milliliters of 0.02M glycine-HCl buffer, pH 3, for about one hour, after which the dialysate was replaced by a fresh one thousand milliliter sample of buffer. The glucoamylase is then diluted 1:70 with 0.02M glycine-HCl, pH 3 to approximate the concentration of the recovered modified enzyme. The control solution for this assay is prepared by adding fourteen milliliters of 0.005M tris, pH 9.1, four milliliters of 0.02M glycine-HCl buffer at pH 3.0 and two milliliters of 0.1M TME. The sample showed no native esterase activity toward TME substrate. The final pH of the control and native assay solution is 6.7.

To determine the level of esterase activity shown by the modified protein prepared according to the present invention, the following procedure is used.

The assay sample is prepared as follows: Fourteen milliliters of 0.005M tris buffer, pH 9.1, and 2 milliliters of 0.1M TME substrate are mixed with 4 milliliters of modified protein.

The control solution is made by adding 14 milliliters of 0.005M tris buffer, pH 9.1, to 2 milliliters of 0.1M TME and 4 milliliters of 0.02M glycine-HCl, pH 3.0, which is the column eluant. The final pH of the control and assay solution is 6.7.

The high pressure liquid chromatography column for the assay are as follows: The column is packed with Baker Bonded Phase Carboxyl, Baker Chemical Co. support which is a carboxyl silane bonded to silica gel. The particle size is about 40 millimicrons. The column eluant is 0.03M acetate buffer, at pH 6. The flow rate is 4 milliliters per minute for a 27 centimeter by 0.3 centimeter column. Twenty microliters of sample is injected and the peak height for tryptophan detected at 254 nm is recorded. Next, the control is injected. After collecting at least four data points for both sample and control, the activity is calculated from a plot of the concentration of tryptophan versus time. The assay results are as follows:

|  | Substrate TME (U/gm) |
| --- | --- |
| Initial Activity | 0.00 |
| Final Activity | 1.1 |

The results show that the modified enzyme-like protein of PART D exhibits activity with respect to esterase substrate TME where no activity was previously detected in the native enzyme. This illustrates the conversion of one genus of enzymatic protein, a glucoamylase to another genus of protein, an enzymatically active esterase-like protein.

EXAMPLE 5

PART A

Preparation of Immobilized Model Enzyme Inhibitor Column

A glass walled chromatography column of about 7.5 centimeters length and about 1.5 centimeters interior diameter is used in the procedure. An immobilized inhibitor, L-tryptophanagarose gel, purchased from Sigma Company, No. T-0137, lot 8OF-9610, is stored in 0.5M NaCl solution at about zero degrees centigrade until used.

To prepare the column for acceptance of the native protein, the column is packed about 3.8 cm. high with immobilized inhibitor. After the column is packed, the column is purged of possible contaminants as follows: A 200 milliliter aliquot of distilled water is flushed through the column at a rate of one milliliter per minute. Next, 500 milliliters of 0.1M carbonate buffer, containing 0.5M NaCl, at pH 10 is flushed through the column at one milliliter per minute. Next, 500 milliliters of 0.1M sodium acetate buffer, at pH 4, containing 0.5M NaCl is flushed through the column at one milliliter per minute. A final five hundred milliliter wash of 2 molar urea solution is flushed through the column.

PART B

Partial Denaturation of the Protein & Binding to the Inhibitor

A fresh one percent solution of bovine serum albumin (BSA) is prepared by dissolving 0.2 grams of bovine serum albumin essentially fatty acid free, from Sigma Company, No. A 7511, lot 9OF-9315 in 20 milliliters of distilled water. The absorbance at 280 nm is measured and is 6.43. The concentration of the BSA is determined in accordance with the teachings of D. M. Kirschenbaum in *Int. J. Peptide Res*, 5, 1973, pages 49–62. Using the absorbance coefficient of 6.62 for a one percent solution, the concentration of the solution is about 9.7 milligrams per milliliter.

The column of PART A is filled with a flowing stream of 0.1 M actate buffer at pH 4.4 flowing at one milliliter per minute, which acts as the denaturing agent solution. Two milliliters of the one percent BSA solution is injected at the head of the column. By so injecting, the BSA is brought to a lowered pH and under such low pH, partially denatured as it flowed onto the column.

The eluant from the column is monitored at 254 nm. When that portion of the BSA not binding to the immobilized inhibitor eluted from the column, it is collected and by the above method, is determined to contain about 16 milligrams. Accordingly, about 3.4 milligrams of the BSA is bound to the inhibitor on one exposure to the column.

PART C

Cross-Linking

The output of the column of PART B is connected to a recirculating pump. The output of the pump is connected to the head of the column to form a closed recirculation flow loop. Next 20 microliters of eight percent glutaraldehyde from Polysciences, Inc., Cat. No. 216, lot 4-1462, is added to 25 milliliters of the 0.01M acetate buffer at pH 4.4. The glutaraldehyde solution is injected onto the column and recirculated for about 90 minutes.

PART D

Collection of the Modified Protein

The recirculating system of PART C is disconnected and a 0.02M glycine-HCl buffer at pH 3.0 is pumped through the column now containing the inhibitor bound, stabilized modified protein, at one milliliter per minute. After about 15 minutes, modified protein began eluting from the column. The eluant is collected as the modified protein is eluting from the column. The collected modified protein is raised from pH 3 to about pH 6.9 to stabilize the protein structure, by the addition of one milliliter of 0.1M tris buffer, pH 7.5, to nine milliliters of eluant. A total of about 0.3 milligrams of modified protein is collected.

PART E

Results

The following activity with respect to substrate for esterase enzyme is recorded from a sample of modified protein prepared according to the invention.

A portion of the eluant solution of modified protein is analyzed for esterase enzymatic activity by high pressure liquid chromatography as follows:

The assay sample is prepared as follows: Sixteen milliliters of 0.1M tris buffer, pH 7.7, and 2 milliliters of 0.1M N-alpha-benzoyl-L-arginine ethyl ester (BAEE) substrate are mixed with 2 milliliters of modified protein.

The control solution is made by adding 16 milliliters of 0.1M tris buffer, pH 7.7 to 2 milliliters of 0.1M BAEE and 2 milliliters of 0.02M glycine-HCl which is the column eluant which is adjusted to pH 6.9 with tris buffer at pH 7.5.

The high pressure liquid chromatography column conditions for the assay are as follows: The column is packed with CM glycophase support from Pierce Chemical Co., which is a hydrophilic, nonionic carbohydrate layer covalently bound to controlled pore size glass having carboxyl methyl side chains. The particle size is about 125-177 microns and the pore size is about 200 angstroms. The column eluant is 0.005M tris buffer, at pH 8.1, containing 0.05M NaCl. The flow rate is 1.75 milliliters per minute for a 27 centimeter by 0.3 centimeter column. Twenty microliters of sample is injected and the peak height for the benzoyl-L- arginine detected at 254 nm is recorded. Next, the control is injected. After collecting at least four data points for both sample and control, the activity is calculated from plot of the concentration of benzoyl-L-arginine versus time. The assay results are as follows:

|  | Substrate BAEE (U/gm) |
|---|---|
| Initial Activity | 0.00 |
| Final Activity | 4.3 |

The results show that the modified esterase-like protein of PART D exhibits activity with respect to esterase substrate BAEE where no activity was previously detected in the native BSA protein. This illustrates the conversion of one genus of nonenzymatic protein, an albumin, to another genus of protein, an enzymatically active esterase-like protein.

EXAMPLE 6

PART A

Preparation of Immobilized Model Enzyme Inhibitor Column

A glass walled chromatography column of about 7.5 centimeters length and about 1.5 centimeters interior diameter is used in the procedure. An immobilized inhibitor, L-tryptophanagarose gel, purchased from Sigma Company, No. T-0137, lot 8OF-9610, is stored in 0.5M NaCl solution at about zero degrees centigrade until used.

To prepare the column for acceptance of the native protein, the column is packed about 3.8 cm. high with immobilized inhibitor. After the column is packed, the column is purged of possible contaminants as follows: A 200 milliliter aliquot of distilled water is flushed through the column at a rate of one milliliter per minute. Next, 500 milliliters of 0.1M carbonate buffer, containing 0.5M NaCl, at pH 10 is flushed through the column at one milliliter per minute. Next, 500 milliliters of 0.1M sodium acetate buffer, at pH 4, containing 0.5M NaCl is flushed through the column at one milliliter per minute. A final five hundred milliliter wash of 2 molar urea solution is flushed through the column.

PART B

Partial Denaturation of the Protein & Binding to the Inhibitor

A fresh one percent solution of bovine serum albumin (BSA) is prepared by dissolving 0.2 grams of bovine serum albumin essentially fatty acid free, from Sigma Company, No. A 7511, lot 9 OF-9315 in 20 milliliters of distilled water. The absorbance at 280 nm is measured and is 7.69. The concentration of the BSA is determined in accordance with the teachings of D. M. Kirschenbaum in *Int. J. Peptide Res,* 5, 1973, pages 49–62. Using the absorbance coefficient of 6.62 for a one percent solution, the concentration of the solution is about 11.6 milligrams per milliliter.

Prior to the addition of the BSA to the column, one hundred microliters of 0.01M 2-mercaptoethanol, in deionized water, is added to ten milliliters of freshly prepared one percent BSA solution. The resultant solution of BSA and 2-mercaptoethanol denaturing agent is stirred gently for about one hour at room temperature to partially denature the native protein.

The column of PART A is filled with a flowing stream of 0.01M acetate buffer at pH 4.4 flowing at one milliliter per minute, which also acts as the denaturing agent solution. Two milliliters of the one percent BSA and 2-mercaptoethanol solution is injected at the head of the column. By so injecting, the BSA is brought to a lowered pH and under such low pH and exposure to the 2-mercaptoethanol is partially denatured.

The eluant from the column is monitored at 280 nm. When that portion of the BSA not binding t the immobilized inhibitor eluted from the column, it is collected and by the above method, is determined to contain about 18.9 milligrams. Accordingly, about 4.3 milligrams of the BSA is bound to the inhibitor on one exposure to the column.

PART C

Cross-Linking

The outlet of the column of PART B is sealed off. The column is allowed to stand for seventeen hours at pH 4.4 to allow disulfide relinkage for cross-linking.

PART D

Collection of the Modified Protein

After about 17 hours the eluant was changed to 0.02.M glycine-HCl buffer, pH 3.0 and the eluting modified protein collected.

PART E

Results

The following activity with respect to substrate for esterase enzyme is recorded from a sample of modified esterase-like protein prepared according to the invention.

A portion of the eluant solution of modified protein is analyzed for esterase enzymatic activity by high pressure liquid chromatography as follows:

The assay sample is prepared as follows: Fourteen milliliters of 0.01M tris buffer, pH 7.8, and 2 milliliters of 0.1M N-alpha-benzoyl-L-arginine ethyl ester (BAEE) substrate are mixed with 4 milliliters of modified protein.

The control solution is made by adding 14 milliliters of 0.01M tris buffer, pH 7.8 to 2 milliliters of 0.1M BAEE and 4 milliliters of 0.02M glycine-HCl, pH 3.0, which is the column eluant. The final pH of the control and assay solution is 7.7.

The conditions for the assay are as follows: The column is packed with CM glycophase support from Pierce Chemical Co. which is a hydrophilic, nonionic carbohydrate layer covalently bound to controlled pore size glass having carboxyl methyl side chains. The particle size is about 125-177 microns and the pore size is about 200 angstroms. The column eluant is 0.005M tris buffer, at pH 8.1, containing 0.05M NaCl. The flow rate is 1.75 milliliters per minute for a 27 centimeter by 0.3 centimeter column. Twenty microliters of sample is injected and the peak height for the benzoyl-L- arginine detected at 254 nm is recorded. Next, the control is injected. After collecting at least four data points for both sample and control, the activity is calculated from a plot of the concentration of benzoyl-L-arginine versus time. The assay results are as follows:

| | Substrate BAEE (U/gm) |
|---|---|
| Initial Activity | 0.00 |
| Final Activity | 8.4 |

The results show that the modified esterase-like protein of PART D exhibits activity with respect to esterase substrate BAEE where no activity was previously detected in the native BSA protein. This illustrates the conversion of on genus of nonenzymatic protein, an albumin, to another genus of protein, an enzymatically active esterase-like protein.

EXAMPLE 7

PART A

Preparation of Immobilized Model Enzyme Inhibitor Column

A glass walled chromatography column of about 3.8 centimeters length and about 5 centimeters diameter is used in the procedure. The inhibitor, cellobiose, is immobilized on a solid, organic water insoluble support comprising an agarose based, linear, cross-linked polysaccharide having alternating residues of D-galactose and 3, 6 anhydro-L-galactose. The immobilization support is available from Pharmacia Fine Chemicals under the name Sepharose 4B Gel.

The column material is prepared in accordance with the process outlined by Sunberg and Porath in *J. of Chromatography*. The procedure is as follows:

Twenty-five grams of Sepharose 4B Gel is washed on a glass filter-funnel with 2 liters of distilled deionized wate and suction-dried for five minutes under vacuum. To the suction-dried gel is added 25 milliliters of 1, 4-butanediol diglycidyl ether and 25 milliliters of 0.6M NaOH containing 2 milligrams of sodium borohydride per milliliter of solution. The resulting suspension is shaken for five hours on an Eberbach shaker at low speed.

After five hours the suspension is washed on a glass filter-funnel with 750 milliliters of distilled, deionized water; then 750 milliliters of 0.02M sodium phosphate buffer, pH 7.5; 750 milliliters of 0.001M tris-HCl buffer, pH 7.0; 750 milliliters of 0.02M glycine-HCl buffer, pH 3.0 and finally 750 milliliters of 0.05M sodium carbonate buffer, pH 10.0 and suction-dried for 5 minutes.

To the suction-dried gel is added 25 milliliters of a 2% D(+) cellobiose solution. The cellobiose solution is made from 500 mg of cellobiose in 25 milliliters of 0.05M sodium carbonate buffer, pH 10 with the cellobiose from Sigma Chemical Co., No. C-7252, lot No. 11OF-0656. The cellobiose-gel solution is shaken at slow speed for 16 hours.

After 16 hours the suspension is washed on a glass filter-funnel with 750 milliliters of 0.05M sodium carbonate buffer, pH 10.0; 750milliliters of distilled deionized water; 750 milliliters of 0.001M tris-HCl buffer, pH 7.0; 750 milliliters of 0.02M glycine-HCl, pH 3.0 and finally 750 milliliters of 0.05M sodium carbonate buffer, pH 9.5. The gel is suction-dried under vacuum for five minutes.

Twelve and one-half grams of the suction dried material is added to 20 milliliters of 2.0M ethanolamine solution. The ethanolamine is made by adding 2.54 milliliters of 95% ethanolamine to sufficient 0.05M sodium carbonate buffer, pH 9.5, to make 20 milliliters volume. The gel-ethanolamine solution is shaken for five hours and then washed on a glass filter-funnel as follows, in the order given, 500 milliliters of 0.05M sodium carbonate buffer, pH 9.5; 500 milliliters of 0.02M sodium phosphate buffer, pH 7.5; 500 milliliters of 0.001M tris-HCl buffer, pH 7.0 and 500 milliliters of distilled deionized water. The gel is next suction-dried under vacuum, resuspended in distilled deionized water and stored under refrigeration until the column is packed.

The 3.8×1.5 centimeter column is fully wet packed with the inhibitor gel and the packed column is washed as follows, in the order given, 200 milliliters of 0.02M sodium carbonate buffer, pH 10.0; 200 milliliters of distilled deionized water; 200 milliliters of 0.02M glycine-HCl buffer, pH 3.0 and 200 milliliters of 0.02M sodium phosphate buffer, pH 8.0.

PART B

Partial Denaturation of the Protein and Binding to the Inhibitor

A fresh 0.4% bovine catalase, systematic name hydrogen-peroxide oxidoreductase, solution is prepared by dissolving 0.04 grams of crystalline bovine catalase, from Sigma Chemical Co., No. C-40, Lot No. 100F-7275, in 10 milliliters of distilled deionized water. The solution is stirred for 15 minutes at room temperature to dissolve the catalase. The 280 nm absorbance is 5.71. The actual number of milligrams of catalase present in the solution is calculated using 12.9 at 280 nm as the absorbance coefficient for a 1% solution, as disclosed in *Int. J. Peptide Protein Res.*, 5, 1973, p. 53 by D. M. Kirschenbaum. The calculated protein concentration is 4.43 milligrams per milliliter. Then the pH of the solution is lowered to 3 by titrating with 0.1 N HCl and is maintained at 3 for one hour. Then 20 microliters of 0.1M B-mercaptoethanol is slowly added over 2 hours with stirring.

Two milliliters of the catalase solution is injected onto the column adding 8.86 milligrams of protein to the inhibitor column.

As protein began eluting, indicating incomplete binding, the eluant is collected. Thirty milliliters of material is collected with an absorbance of 0.078 yielding 1.83 milligrams of collected catalase. Thus, about 7 milligrams of catalase are bound to the inhibitor on the column.

PART C

Cross-Linking

A cross-linking agent solution is prepared by dissolving 0.035 grams of dimethyl suberimidate dihydrochloride, from Sigma Chemical Co. No. D-763, lot No. 110F-0322, in twenty five milliliters of 0.02M sodium phosphate buffer, pH 8. The outlet of the column of PART B is connected to a recirculating pump. The outlet of the pump is connected to the head of the column to form a closed recirculation flow loop. Next the twenty five milliliters of cross-linking agent is recirculated through the column for about one hour at a flow rate of one milliliter per minute.

PART D

Collection of the Modified Protein

The recirculating system of PART C is disconnected and a 0.02M glycine-HCl buffer at pH 3.0 is pumped through the column now containing the inhibitor bound, stabilized modified protein, at one milliliter per minute. After about five minutes, modified protein began eluting from the column. About 15 milliliters of eluant is collected before the modified protein stopped eluting.

The absorbance at 280 nm is determined as in PART B to be 0.249 thus about 2.9 milligrams of modified protein is found to be collected.

Next, the eluant is changed to 0.02M sodium carbonate buffer, pH 10.0 and five milliliters of additional eluant are collected, bearing 0.27 milligrams additional modified protein.

PART E

Results

The following activity with respect to substrate for a beta-glucosidase enzyme is recorded from a sample of modified beta-glucosidase-like protein prepared according to the invention in PARTS A-D.

A portion of the eluant collected in PART D is analyzed for beta-glucosidase enzymatic activity as follows:

The activity is determined spectrophotometrically using a CARY-14 RI spectrophotometer by measuring the change in absorbance as a function of time on a scale of 0 to 0.1 absorbance units.

The reaction mixture is prepared as follows: 2.4 milliliters of 0.02M sodium phosphate buffer, pH 7.0 and 0.5 milliliters of 0.014M p-nitrophenyl beta-D glucoside substrate (NPG) are mixed with 0.1 milliliters of the modified protein of PART D collected a pH 3.0. The substrate solution is prepared by dissolving 0.042 grams of substrate in 10 milliliters of distilled deionized water.

The control mixture is prepared by mixing 2.4 milliliters of 0.02M sodium phosphate buffer pH 7.2 and 0.5 milliliters of distilled deionized water with 0.1 milliliters of modified protein of PART D.

A second control solution is prepared by mixing 2.4 milliliters, of 0.02M sodium phosphate buffer, pH 7.1 and 0.5 milliliters of 0.014M NPG with 0.1 milliliters of distilled deionized water. The absorbance change at 405 nm is recorded for five minutes in both controls and the reaction mixture. The final pH for all three solut.rons is 7.1.

The absorbance change for the first control is 0.001 in 4.5 minutes. The second control showed no absorbance change indicating no rate due to substrate hydrolysis.

The activity observed is found to be biphasic. The rate for the first minutes is significantly faster than the sustained rate. The initial absorbance change for the reaction mixture is 0.0025 for one minute or phase one of the activity measure and 0.0017 for 4.5 minutes for the sustained rate or phase two activity.

The following formula is used t calculate the enzymatic activity of the modified glucosidase-like protein prepared according to the invention in PARTS A-D.

$$\text{units/g} = \frac{(\text{change absorbance/min.})(\text{sample size in liters})(10^6 \text{ umoles/mole})}{(13 \times 10^3 \text{ liters/mole})(\text{g of modified protein in reaction mixture})}$$

Wherein: $13 \times 10^3$ liters/mole is the extinction coefficient for p nitrophenol as determined for the given pH and buffer system.

The assay results are as follows:

|  | Substrate<br>NPG (U/g) |
|---|---|
| Initial | 0.00 |
| Phase One | 30.0 |
| Phase Two | 4.5 |

Because catalase precipitates readily, a second assay method is employed using a CARY 14-RI spectrophotometer. The isosbestic point test for p-nitrophenyl B-D glucoside is used to determine if the modified glucosidase-like protein would precipitate at pH 7.1, the pH of the assay. The isosbestic point of p-nitrophenyl B-D glucoside and p-nitrophenol at pH 7.1 in 0.02M sodium phosphate buffer is 331.8 nm.

Two tandem spectrophotometer cuvettes are used. The path length of each cell is 0.5 centimeters. The reference tandem cuvette is filled with distilled deionized water on one side. The second side is filled with 1.2 milliliters of 0.02M sodium phosphate buffer, pH 7.2; 0.2 milliliters of 0.014M p-nitrophenyl B-D glucoside and 50 microliters of distilled deionized water.

The sample tandem cuvette is filled on one side with distilled deionized water and on the other side with 1.2 milliliters of 0.02M sodium phosphate buffer, pH 7.2; 0.2 milliliters of 0.014M p-nitrophenyl beta-D glucoside and 50 microliters of modified protein solution.

During the experiment no change in absorbance at 331.8 nm is observed. Since no increase in absorbance is observed no contribution to the measured reaction rate is due to modified protein precipitation.

To illustrate that native bovine catalase shows no measurable catalytic activity towards glucosidase substrate the following procedure is performed. A solution of native bovine catalase, from Sigma Chemical Company, No. C-40, Lot #100F-7275, is assayed against p-nitrophenyl-beta-D glucoside (NPG) substrate to determine if it is enzymatically active with respect to NPG. The native bovine catalase solution is prepared by dissolving 0.1 gram of the catalase in 10 milliliters of distilled, deionized water. The resultant one percent solution is stirred for 15 minutes at room temperature to dissolve the catalase. Then, the pH of the solution is lowered to 3 by titrating with 0.1N HCl. This solution is dialyzed in 0.02M glycine-HCl buffer, at pH 3.0, for about one hour. After one hour the dialysate is replaced by a fresh 1000 milliliter aliquot of buffer. A Spectra/Por (registered trademark) dialysis tubing is used having a molecular weight exclusion range of 12-14,000 daltons. The dialyzed catalase is then diluted 1:50 with 0.02M glycine-HCl buffer, pH 3, to approximate the concentration of the recovered modified glucosidase-like protein recovered and tested above. The absorbance at 280 nm is measured as 0.251. Using the absorbance coefficient value of 12.9 (as disclosed above in the Int. J. Peptide Protein Res. article at 5, 1973, p. 53) the concentration of the solution is about 0.2 milligrams of modified protein per milliliter of solution.

The assay is done spectrophotometrically using a CARY-14 RI spectrophotometer by measuring the change in absorbance as a function of time. The CARY-14 instrument has an established baseline drift of less than 0.001 absorbance units per hour.

A native catalase enzyme assay mixture is prepared as follows: 2.4 ml of 0.02M sodium phosphate buffer, at pH 7.1 and 0.5 milliliters of 0.014M NPG substrate are admixed with 0.1 milliliters of the dialyzed native catalase, at pH 3.0. The NPG substrate solution is prepared by dissolving 0.042 grams of NPG substrate in 10 milliliters of distilled, deionized water.

A control solution is prepared by mixing 2.4 milliliters of 0.02M sodium phosphate buffer, at pH 7.1 and 0.5 milliliters of NPG substrate with 0.1 milliliters of 0.02M glycine-HCl buffer, at pH 3.0.

The final pH of both solutions is 7.1. The absorbance change at 405 nm is recorded for five minutes for both solutions. The absorbance change for the native catalase enzyme mixture and the control mixture is the same, 0.001 absorbance units in five minutes. Therefore, the native bovine catalase has no detectable initial beta-glucosidase activity toward NPG substrate.

Accordingly, the procedure shows that native bovine catalase exhibits no measurable catalytic activity with respect to glucosidase substrate NPG.

EXAMPLE 8

PART A

Preparation of Immobilized Model Enzyme Inhibitor Column

A glass walled chromatography column of about 3.8 cm. length and about 1.5 cm. interior diameter is used in the procedure. The immobilized inhibitor, cellobiose, gel is prepared as described in Example 7. To prepare the column for acceptance of the native protein, the column is packed about 3.8 cm. high with immobilized inhibitor. After the column is packed, the column is purged of possible contaminants by washing the column as follows: 200 milliliters of 0.02M sodium carbonate buffer, pH 10.0; 200 milliliters of distilled, deionized water; 200 milliliters of 0.02M glycine-HCl buffer, pH 3.0 and finally 200 milliliters of 0.001M Tris HCl, pH 7.0.

PART B

Partial Denaturation of the Protein and Binding to the Inhibitor

Two and one-half milliliters of glucoamylase, an alpha-glucosidase having the systematic name alpha-1,4-glucan glucohydrolase, (purchased from Sigma Chemical Co. as glucoamylase No. A-3514, Lot 28C-0442) is diluted with 7.5 ml of distilled, deionized water and dialyzed against 0.001M tris-HCl buffer, pH 7.0, for about 16 hours. As received from Sigma Chemical Company, 100 mg of the glucoamylase is suspended in about ten milliliters of 3.2M ammonium sulfate solution, pH 6. The glucoamylase enzyme is dialyzed using a dialysis tubing having a molecular weight cut off of 12-14,000 daltons.

The concentration of the native glucoamylase enzyme solution is determined in accordance with the teachings of D. M. Kirschenbaum in *Analytical Biochemistry* 82, pages 83-100, 1977. The absorbance at 280 nm is measured as 2.78. Using the absorbance coefficient value of 13.6, the concentration of the solution is about 2.1 milligrams of native glucoamylase enzyme per milliliter of solution.

Prior to the addition of the dialyzed glucoamylase at pH 7.0 to the inhibitor column, 20 microliters of 0.1M 2-mercaptoethanol, in distilled, deionized water, is added to ten milliliters of the dialyzed glucoamylase. The resultant solution of glucoamylase and 2-mercaptoethanol denaturing agent is stirred gently for 60 minutes, at room temperature, to partially denature the native enzyme.

The column of PART A is filled with a flowing stream of 0.001M tris-HCl buffer, at pH 7.0, flowing at 0.5 milliliters per minute. Five milliliters of the glucoamylase and 2-mercaptoethanol solution is injected at the head of the column.

As protein began eluting, indicating incomplete binding, the eluant is collected. Fifteen milliliters of protein material is collected, with an absorbance of 0.03, yielding 0.33 milligrams of collected glucoamylase. Thus, about ten milligrams of glucoamylase are bound to the inhibitor on the column.

PART C
Cross-linking

A cross-linking agen solution is prepared by dissolving 0.044 g of dimethyl suberimidate dihydrochloride, from Sigma Chemical Company, No. D-7636, lot 31F-0225, in 25 milliliters of 0.005M tris-HCl buffer, pH 7.5. The outlet of the column of PART B is connected to a recirculating pump. The outlet of the pump is connected to the head of the column to form a closed recirculation flow loop. The 25 milliliters of cross-linking agent is recirculated through the column for about one hour at a flow rate of 0.5 milliliters per minute.

PART D
Collection of the Modified Protein

The recirculating system of PART C is disconnected and a 0.02M glycine-HCl buffer, at pH 3.0, is pumped through the column now containing the inhibitor-bound, stabilized modified enzyme-like protein, at 0.5 milliliter per minute. After about five minutes, modified protein began eluting from the column. About sixteen milliliters of eluant is collected before the modified protein stopped eluting.

The absorbance at 280 nm is determined as in PART B to be 0.764, thus, about 8.9 milligrams of modified protein is found to be collected.

PART E
Results

The following activity with respect to substrate for a beta-glucosidase enzyme is recorded from a sample of modified beta-glucosidase-like protein prepared according to the invention in PARTS A-D.

A portion of the eluant collected in PART D is analyzed for beta-glucosidase enzymatic activity as follows:

The activity is determined spectrophotometrically using an ACTA III spectrophotometer (Beckman Instrument Co.) by measuring the change in absorbance as a function of time.

The reaction solution is prepared as follows: 0.7 milliliters of 0.002M sodium acetate buffer, pH 5.0 and 0.2 milliliters of 0.014M p-nitrophenyl beta-D glucoside substrate (NPG) are mixed with 0.1 milliliters of the modified betaglucosidase protein of PART D, collected at pH 3.0. The substrate solution is prepared by dissolving 0.042 g of substrate in 10 milliliters of distilled, deionized water.

The control solution is prepared by mixing 0.7 milliliters of 0.002M sodium acetate buffer, pH 5.0 and 0.2 milliliters of 0.014M NPG substrate with 0.1 ml of 0.02M glycine-HCl buffer, at pH 3.0. The final pH of the control and assa solution is 5.0.

After incubating both the reaction and control solutions for 15 minutes at 30° C., in a dry heat temperature block, the reaction is stopped by the addition of on milliliter of 0.02M sodium carbonate.

The absorbance of the control solution is 0.028, when measured at 405 nm, and the absorbance of the reaction solution is 0.043. This yields an absorbance change after 15 minutes of 0.015.

The following formula is used to calculate the enzymatic activity of the modified beta-glucosidase-like protein prepared according to the present invention.

$$\frac{(\text{change absorbance/min.})(\text{sample size in liters})(10^6 \text{ umoles/mole})}{(16.2 \times 10^3 \text{ liters/mole})(\text{milligrams of modified protein in reaction mixture})}$$

Wherein: $16.2 \times 10^3$ liters/mole is the extinction coefficient for p-nitrophenol a determined for the given pH and buffer system.

The assay results are as follows:

|  | Substrate NPG (U/g) |
|---|---|
| Initial Activity | 0.00 |
| Final Activity | 2.2 |

The results show that the modified beta-glucosidase-like protein of PART D exhibits activity with respect to beta-glucosidase substrate NPG where no activity toward NPG is previously detected in the native glucoamylase.

To verify that native glucoamylase shows no natural beta-glucosidase activity the following procedure was performed. Native glucoamylase is dialyzed against 0.001M tris-HCl buffer at pH 7.0 overnight. The glucoamylase is dialyzed using a dialysis tubing having a molecular weight cutoff of 12–14,000 daltons.

The native glucoamylase reaction mixture is prepared as follows: 0.7 milliliters of 0.002M sodium acetate buffer, at pH 5.0 and 0.2 milliliters of 0.014M NPG are mixed with 0.1 ml of the dialyzed native glucoamylase.

The control mixture for this assa is prepared by mixing 0.7 milliliters of 0.002M sodium acetate buffer, at pH 5.0 and 0.2 milliliters of 0.014 NPG substrate with 0.1 ml of 0.001M tris-HCl buffer, at pH 7.0. The final pH of the control and native reaction mixture is 5.0.

After incubating both the reaction and control mixtures for 15 minutes at 30° C., in a dry heat temperature controlled block, the assay is stopped by the addition of one milliliter of 0.02M sodium carbonate.

The absorbance of the control and reaction mixture is 0.026 when measured at 405 nm. Therefore, there was no net change in absorbance and consequently no activity measured for the native glucoamylase, with respect to the beta-glucosudase substrate NPG.

Having described the invention, what is claimed is:

1. A process for chemically altering the substrate specificity of a native protein to produce a predetermined modified enzyme-like protein comprising:
   a. selecting an enzymatically active protein to be modeled;
   b. immobilizing an inhibitor of said predetermined enzyme model on a solid support:
   c. partially denaturing said native protein and d. cross-linking said partially denatured native protein in the presence of said support immobilized inhibitor of said model enzyme.

2. The process of claim 1 wherein said model enzyme inhibitor is covalently immobilized on said solid support.

3. The process of claim 1 wherein said solid support is a carbohydrate.

4. The process of claim 3 wherein said carbohydrate is an agarose gel.

5. The process of claim 1 wherein said native protein is partially denatured by forming an aqueous solution of said native protein and maintaining said aqueous solution at a temperature and for a time sufficient to partially denature said native protein.

6. The process of claim 1 wherein said native protein is partially denatured by admixing said native protein with water to form an aqueous solution and admixing the resulting solution with a denaturing agent.

7. The process of claim 6 wherein said denaturing agent is an inorganic acid.

8. The process of claim 6 wherein said denaturing agent is a water-miscible organic solvent.

9. The process of claim 6 wherein said denaturing agent is an inorganic salt.

10. The process of claim 1 wherein said support is a water insoluble support.

11. The process of claim 1 wherein said partially denatured protein is contacted with s id immobilized inhibitor for said model enzyme by flowing said partially denatured protein through a hollow column containing said immobilized model enzyme inhibitor.

12. The process of claim 1 wherein said partially denatured protein is contacted with said immobilized model enzyme inhibitor by soaking said partially denatured protein in an aqueous media containing said immobilized model enzyme inhibitor.

13. The process of claim 1 wherein said partially denatured protein is cross-linked by flowing an aqueous solution of cross-linking agent through a hollow column containing the inhibitor bound partially denatured protein.

14. The process of claim 1 wherein said partially denatured protein is contacted with said cross-linking agent by soaking said inhibitor bound partially denatured protein in an aqueous media containing said cross-linking agent.

15. A process to produce a modified enzyme-like protein comprising:
    a. selecting an enzymatically active protein to be modeled;
    b. selecting a second protein to be modified to model the activity characteristics of said enzymatically active protein;
    c. selecting an inhibitor for said enzymatically active protein;
    d. immobilizing said selected model enzyme inhibitor on a solid support;
    e. partially denaturing said second protein; and
    f. cross-lining said partially denatured protein in the presence of said support immobilized model enzyme inhibitor.

16. The process of claim 15 wherein said model enzyme inhibitor is covalently immobilized on said solid support.

17. The process of claim 15 wherein said solid support is a carbohydrate.

18. The process of claim 17 wherein said carbohydrate is an agarose gel.

19. The process of claim 15 wherein said second protein is partially denatured by forming an aqueous solution of said second protein and maintaining said aqueous solution at a temperature and for a time sufficient to partially denature said second protein.

20. The process of claim 15 wherein said second protein is partially denatured by admixing said second protein with water to form an aqueous solution and admixing the resulting solution with a denaturing agent.

21. The process of claim 20 wherein said denaturing agent is an inorganic acid.

22. The process of claim 20 wherein said denaturing agent is a water-miscible organic solvent.

23. The process of claim 20 wherein said denaturing agent is an inorganic salt.

24. The process of claim 15 wherein said solid support is a water insoluble support.

25. The process of claim 15 wherein said partially denatured second protein is contacted with said immobilized model enzyme inhibitor by flowing said partially denatured second protein through a hollow column containing said immobilized model enzyme inhibitor.

26. The process of claim 15 wherein said partially denatured second protein is contacted with said immobilized model enzyme inhibitor by soaking said partially denatured second protein in an aqueous media containing said immobilized model enzyme inhibitor.

27. The process of claim 15 wherein said partially denatured second protein is cross-linked by flowing an aqueous solution of cross-linking agent through a hollow column containing said inhibitor bound partially denatured protein.

28. The process of claim 15 wherein said partially denatured second protein is contacted with said cross-linking agent by soaking said inhibitor bound partially denatured second protein in an aqueous media containing said cross-linking agent.

29. The product of the process of claim 1.

30. The product of the process of claim 15.

* * * * *